April 25, 1972 W. E. LAMMERTS Plant Pat. 3,129
ROSE PLANT
Filed May 11, 1970
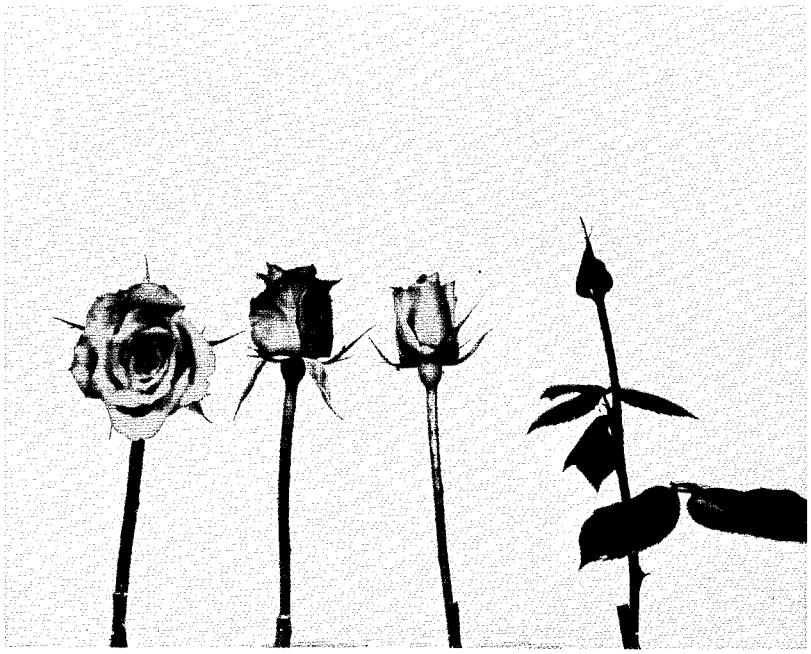
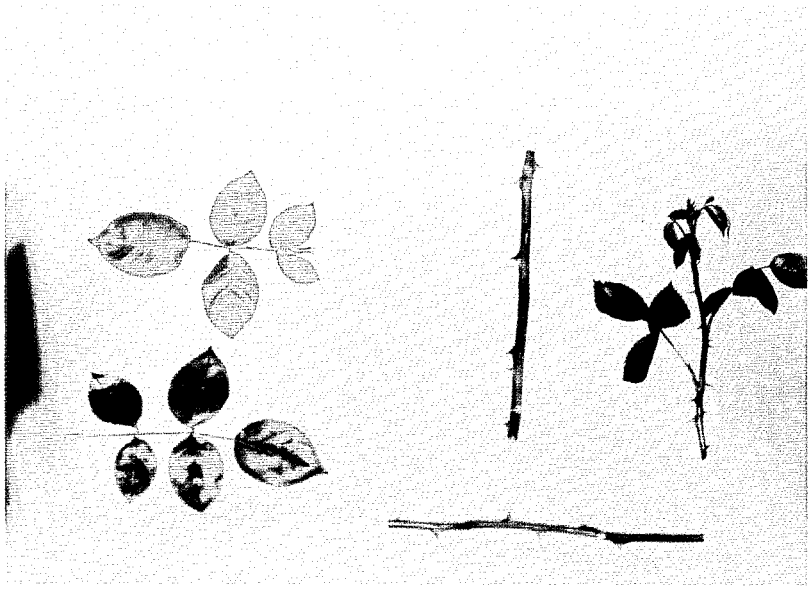
INVENTOR.
WALTER E. LAMMERTS
BY Rummler & Snow
Attys

United States Patent Office

Plant Pat. 3,129
Patented Apr. 25, 1972

3,129
ROSE PLANT

Walter E. Lammerts, Freedom, Calif., assignor to Germain's, Inc., Los Angeles, Calif.

Filed May 11, 1970, Ser. No. 36,504
Int. Cl. A01h *5/00*
U.S. Cl. Plt.—20 1 Claim

ABSTRACT OF THE DISCLOSURE

A hothouse variety of hybrid tea rose originating as a seeding of Baccara (P.P. 1,367)×Rumba (P.P. 1,919) and distinguished by an improved and more uniform red coloring of its flowers when compared with the seed parent Baccara, particularly at the ¼ to ½ opened stage, and by a much more abundant production of flowers, which bloom from early to late season in the garden and the year around under glass.

BACKGROUND OF THE INVENTION

This new variety of rose plant has resulted from breeding efforts carried on by me at Livermore, Calif., since 1953 with the object of developing a rose which would combine the texture, keeping quality and general color range of Baccara (P.P. 1,367) with increased flower production and improved foliage appearance. The most satisfactory results were obtained by crossing Baccara with the unrelated, very productive, floribunda variety Rumba (P.P. 1,919) and the seedling originator of this new variety, discovered in 1965, was selected for testing and asexual propagation because the new plant appeared to combine the desired characteristics of Baccara with the glossy foliage of Rumba. Testing also showed the selected seedling to have the advantageous productivity characteristics of Rumba, and because the distinguishing and sought for features of the breeding efforts remained true from generation to generation of asexual reproduction, this new variety was chosen for commercial production.

Asexual propagation of this new variety was first done at Livermore, Calif., by budding and propagation by the same method as now being done under glass at Livermore, Calif., and in the nursery at Hamilton City, Calif.

DESCRIPTION OF THE DRAWINGS

My new variety of rose plant is illustrated by the accompanying photographic representation in which the upper view shows various stages of bloom development from new bud to the fully opened flower; and the lower view shows the front and back sides of a typical leaf, portions of the mature wood, and a young branch showing the new wood and foliage.

DESCRIPTION OF THE NEW PLANT

The following is a detailed description of my new variety of rose plant with color designations according to the R.H.S. Colour Chart of the Royal Horticultural Society.

*The plant*

Origin: Seedling (#G64001/1H).

Parentage: Seed parent—Baccara (P.P. 1,367). Pollen parent—Rumba (P.P. 1,919).

Classification: Botanic—Hybrid tea. Commercial—Hothouse rose.

Form: Tall, compact bush.

Height: In hothouse—5 to 7 feet; in garden—3 to 4 feet.

Growth: Very vigorous and rapid growth habit both in hothouse and in garden.

Branching: Branches freely, upright and not spreading. "Double breaks" freely.

Strength: Very upright, sturdy, slender stems with good strength for erect carriage of the flower.

Foliage: Quantity—abundant, with leaves spaced about 3 inches apart on the flowering stem.

*Size of leaf.*—5" to 5½" wide x 5¼" to 7" long.

*Shape of leaf.*—Odd pinnate; usually with 5 leaflets, sometimes 7 leaflets. Leaflet shape—oval with mucronate tip and serrate margins. Texture—leathery and smooth. Aspect—glossy. Color—upper side—Yellow Green 147A; under side—Yellow Green 147B but with much more anthrocyanin pigment than Baccara. Size—Apex leaflet—2" to 2¼" wide x 3" to 3½" long; lateral leaflet—1½" wide x 2⅝" long.

*Petioles.*—Length, apex leaflet—¾" to 1"; lateral leaflets—1/16" to ⅛".

*Ribs and veins.*—Prominent, slightly depressed and of lighter green than top side of leaflet.

Rachis: Stipules—Adnate—serrated and tipped with glands. Auricles—sharply pointed at 45° angle.

Spines: Size—on young flowering wood—5/16" to 9/16" long x 3/32" to ⅛" thick at base and 5/16" to 6/16" high. Color—on old wood at base of plant, near Greyed-Orange 177B; on next older wood, from first pinch, near Greyed-Orange174B; on young flowering wood, from Yellow-Green 149A at the tip to Greyed-Orange 176A near center and Greyed-Purple 184B to 184C at base of large spines.

Prickles: On old wood, both spines and prickles occur; on flowering wood, only spines are found. Prickles with a very occasional spine are found on the peduncle of the flower.

*The bud*

Form: Ovoid to Urn shaped. Opens slowly.

Size: When sepals first divide—⅞" to 1" long x ⅞" to 1" wide at base. When ¼ open—1¼" diameter at base; 1 3/16" to 1⅜" in depth.

Color: When sepals first divide, Greyed-Purple 185A; when petals begin to unfurl, Red 45A.

Sepals: Hooded over bud; clasping but opening to cup-shaped before petals begin to unfurl. Sepals curl back as petals open; they are shaped with alternate ones laciniated. Usually two sepals are without laciniations. Color—Inside, Green 139C with white hairs. Outside, Yellow-Green 144A with tinge of anthrocyanin color in the mid-rib.

Calyx: Form—pear shaped. Size—medium, 7/16" to ⅝" wide x 7/16" long. Aspect—smooth.

Peduncle: Strong, well proportioned to stem and flower, slender and upright, with sparse hairs 1 to 2 mm. long and small prickles 1/16" to ⅛" long.

*The flower*

Blooming habit: Continuously and profusely from early spring through late fall. The plant blooms freely in the fall and also in the winter under glass. Flowers are borne singly.

Size: Medium. Diameter 3¼" to 3½"; depth to 1¼" to 1⅜'.

Shape: High center and form does not change as bloom matures.

Petalage: Number of petals, 33 to 42.

*Arrangement.*—Imbricated.

*Form.*—Round. The margin is entire and a small mucronate point is formed at the center of the tip.

*Color.*—Outer petal, from Red 44A to 44B. Base: Yellow 6B. Inside petal, Red 40A. Reverse side—outer petal, Red 53D. Inside petal, Red-Purple 61C.

*Texture.*—Firm. Appearance, velvety.

Petaloids: 9 to 12 in number.

*Size.*—½" to ¾" wide x 5/16" to ⅝" long.

*Color.*—Red 40A with Yellow 6B markings.

Persistence: Excellent, does not dry on plant and petals drop cleanly. Petals stay on the stem 24 to 30 days.

Discoloration: Very slight after full bloom.

Disease resistance: The plant resists mildew and Botrytis as observed in the field at Livermore, Calif., and at Hamilton City, Calif.

Fragrance: Slight aroma of freshly brewed tea.

Lasting quality: On plant—20 to 26 days. As a cut flower—8 to 10 days.

Peduncle: 4" to 5½" long. Color—Yellow-Green 146D.

*Reproductive organs*

Stamens:

*Anthers.*—Irregularly arranged and introrse. Length—1/16" to ⅛". Number—120–156. Color—Yellow-Orange 17A.

*Filaments.*—Attached at base of anthers. Length—3/32" to 3/16". Color—Red 40A.

Pollen: Color—Yellow-Orange 14A to 14B.

Pistils: Number—104–142, Length—7/32" to ½".

Stigmas: Color—Greyed-Yellow 160C.

Characteristics of ovaries: Many, well developed and unattached to each other. Ovaries are covered with white hairs of minute size.

*Fruit*

Fertile at maturity and of round shape.

Color at maturity is Yellow-Orange 23B.

My new variety of rose plant most resembles Baccara (P.P. 1,367), its seed parent. There are many distinctive differences, however, and the most outstanding and noticeable difference is that the color of the outside petals of the flower of the new variety, up to the time the blooms are ¼ to ½ open, is Red 53B whereas the outside petals of Baccara at the same stage are Greyed-Purple 187A to 187B. This difference gives the new variety a clear clean appearance at this stage, whereas, at the same stage. Baccara has a blotched appearance.

My new variety has another important advantage in that its productivity is more than double that of Baccara. My new variety produced 28 flowers over a twelve month period, whereas Baccara produced 13 flowers during the same time. Both varieties were grown under similar conditions for this test and both were budded plants on Manetti understock.

Other noticeable differences of my new variety of rose plant over the parent variety Baccara are found in the peduncle which in Baccara is of Green 143C in color and has about 10 per inch of very small, almost hair size, prickles. The peduncle of the new variety is Yellow-Green 146D in color and has many prickles averaging 19 per inch, of a size clearly visible and some of which are like small ⅛" long thorns.

The thorns of the new variety are larger on flowering wood and much more red at the base than those of Baccara, which have relatively little red at base. The thorns of Baccara are also more slender and average ⅛" less in height than those of the new variety. Also, the leaves of the new variety are glossier, more serrated, less round and more pointed than those of Baccara; carry more anthocyanin on the under side than the leaves of Baccara; and have leaf veins that are more deeply indented than Baccara.

All of the observations upon which the foregoing specification is based were made under greenhouse conditions at Livermore, Calif., and Salina, Calif., and under nursery field conditions at Hamilton City, Calif.

I claim:

1. A new and distinct variety of rose plant substantially as herein shown and described, characterized by the clear, clean appearance of the outer surface of the outer petals of the ¼ to ½ opened flower, as compared with the seed parent Baccara at the same stage; by its doubling of the flower output of Baccara; and by its more vigorous growth habit and more glossy and attractive foliage than either of its parents.

No references cited.

ROBERT E. BAGWILL, Primary Examiner